United States Patent [19]

Schneider et al.

[11] Patent Number: 5,633,434
[45] Date of Patent: May 27, 1997

[54] TRANSGENIC PLANTS DISPLAYING VIRUS AND PHOSPHINOTHRICIN RESISTANCE

[75] Inventors: Rudolf Schneider, Kelkheim/Taunus; Günter Donn, Hofheim am Taunus; Hubert Müllner, Kelkheim/Taunus, all of Germany

[73] Assignee: Hoechst Aktiengesellschaft, Frankfurt, Germany

[21] Appl. No.: 279,706

[22] Filed: Jul. 25, 1994

Related U.S. Application Data

[63] Continuation of Ser. No. 123,699, Sep. 17, 1993, abandoned, which is a continuation of Ser. No. 910,329, filed as PCT/EP91/00130 Jan. 24, 1991, abandoned.

[30] Foreign Application Priority Data

Feb. 2, 1990 [DE] Germany ................................ 4003045

[51] Int. Cl.$^6$ ............................ C12N 5/10; C12N 15/11; C12N 15/33; A01H 5/00
[52] U.S. Cl. .................... 800/205; 800/250; 435/172.3; 435/69.1; 435/193; 435/418; 435/419; 536/23.1; 536/23.2; 536/23.72; 47/58
[58] Field of Search ................................ 800/205, 250; 435/172.3, 69.1, 240.4, 193; 536/23.1, 23.2, 23.72; 47/58

[56] References Cited

U.S. PATENT DOCUMENTS 5,489,520  2/1996  Adams et al. ........................ 435/172.3

OTHER PUBLICATIONS

Finnegan et al. 1994. Biotechnology 12:883–888.
Potrykus. 1990. Bio/Technology 8:535–542.
Tumer et al. 1987. Embo J 6:1181–1188.
De Block et al. 1987. Embo J 6:2513–2518.
Loesch-Fries et al. 1987. Embo J 6:1845–1851.
Weising et al., "Foreign Genes in Plants: Transfer, Structure, Expression, and Applications," *Annu. Rev. Genet.* 1988, 22:421–77.

*Primary Examiner*—David T. Fox
*Assistant Examiner*—Elizabeth C. Kemmerer
*Attorney, Agent, or Firm*—Curtis, Morris & Safford, P.C.

[57] ABSTRACT

Virus genes, for example coat protein genes, which bring about a reduction in the signs of infection by the corresponding virus or bring about virus resistance can be combined with herbicide-resistance genes for the transformation of plants.

A combination of this type facilitates the selection of the transgenic plants. In addition, in practical field cultivation, the vitality of the plants is increased by the virus tolerance, and an improved plant protection is possible owing to the herbicide-resistance gene.

19 Claims, No Drawings

TRANSGENIC PLANTS DISPLAYING VIRUS AND PHOSPHINOTHRICIN RESISTANCE

This application is a continuation-in-part, continuation of application Ser. No. 08/123,699, filed Sep. 17, 1993, now abandoned, which in turn is a continuation of application Ser. No. 07/910,329, filed as PCT/EP91/00130, Jan. 24, 1991, which in turn is abandoned.

BACKGROUND OF THE INVENTION

The synthesis of virus coat protein in plants leads to an enhanced resistance of the plant to the corresponding virus. European Patent Application 0 240 331, for example, describes the preparation of plant cells which contain such a coat protein.

Turner et al. [EMBO J. 6, 1181 (1987)] have carried out the transformation of tobacco and tomato plants with a chimeric gene which codes for the coat protein of alfalfa mosaic virus. The progeny of these is transformed plants which showed a significant reduction in the signs of infection with the corresponding virus, and in some cases even virus resistance.

SUMMARY OF THE INVENTION

It has now been found that such virus genes can be combined with a herbicide-resistance gene, which facilitates the selection of the transgenic plants. At the same time, in practical field cultivation, the vitality of the plants is increased by the virus tolerance, and an improved plant protection is possible owing to the herbicide-resistance gene. It has been generally observed that herbicide application exerts a stimulating effect on growth. The plant transformed according to the invention shows an enhancement of this effect, which makes it possible to achieve an improved plant yield.

Herbicide-resistance genes have already been disclosed. German Offenlegungsschrift 37 16 309 describes the selection of non-fungoid bacteria which are resistant to phosphinothricin. The phosphinothricin-resistance gene can be localized to a fragment 2 kb in size on the DNA of these selectants.

German Offenlegungsschrift 37 37 918 indicates a way of synthesizing the phosphinothricin-resistance gene from the genome of Streptomyces viridochromogenes. Incorporation in gene structures with whose aid transformed plants become resistant to the herbicide is likewise described therein.

The invention thus relates to a gene coding for a virus resistance combined with a herbicide resistance.

The invention is described in detail hereinafter, especially in its preferred embodiments. Furthermore, the invention is defined by the contents of the claims.

DETAILED DESCRIPTION OF THE INVENTION

The genes for virus resistance, especially the virus coat proteins, can be obtained starting from isolated virus RNA by cDNA cloning in host organisms. The preferred starting material for this is the RNA of cucumber mosaic virus, of alfalfa mosaic virus or of brom mosaic virus.

Herbicide-resistance genes can be isolated from bacteria, for example of the genera Streptomyces or Alcaligenes. Preferably used is the phosphinothricin-resistance gene from Streptomyces viridochromogenes (Wohlleben, W. et al., Gene 80, 25–57 (1988)), which can be appropriately modified for expression in plants.

The genes are cloned and sequenced in each case using the vectors pUC19, pUC18 or pBluescript (Stratagene, Heidelberg, Product Information).

The gene is cloned in an intermediate vector with plant promoter. Examples of such vectors are the plasmids pPCV701 (Velten J. et al., EMBO J. 3, 2723–2730 (1984)), pNCN (Fromm H. et al., PNAS 82, 5824–5826 (1985)), or pNOS (an, G. et al., EMBO J. 4, 277–276 (1985)). Preferably used is the vector pDH51 (Pietrzak, M. et al., NAR 14, 5857, (1986)) with a 35S promoter, or the vector pNCN with a Nos promoter.

After subsequent transformation of E. coli, such as, for example, E. coli MC 1061, DH1, DK1, GM48 or XL-1, positive clones are identified by methods known per se (Maniatis et al., Lab. Manual), such as plasmid minipreparation and cleavage with an appropriate restriction enzyme.

These positive clones are then subcloned together into a binary plant vector. The plant vector which can be employed is pGV3850 (Zambrysk, P. et al., EMBO J. 2, 2143–2150 (1983)) or pOCA18 (Olszewski, N., NAR 16, 10765–10782, (1988)). pOCA18 is preferably employed.

The resulting binary plant vectors which contain plant promoters with the attached DNA fragment for the expression of virus coat protein and phosphinothricin resistance in the T-DNA are used to transform plants. This can be carried out by techniques such as electroporation or microinjection. Preferably employed is cocultivation of protoplasts or transformation of leaf pieces with Agrobacteria. For this, the plant vector construct is transferred by transformation with purified DNA or, mediated by a helper strain such as E. coli SM10 (Simon R. et al., Biotechnology 1, 784–791 (1983)), into Agrobacterium tumefaciens such as A282 with a Ti plasmid via triparental mating. Direct transformation and triparental mating were carried out as described in "Plant Molecular Biology Manual" (Kluwer Academic Publisher, Dardrech (1988)).

It is possible in principle to transform all plants with the binary plant vectors carrying the DNA constructed according to the invention. Dicotyledonous plants are preferred, especially productive plants which produce or store starch, carbohydrates, proteins or fats in utilizable amounts in their organs, or which produce fruit and vegetables or which provide spices, fibers and industrially useful products or pharmaceuticals, dyes or waxes and, moreover, fodder plants. As example mention may be made of tomato, strawberry, avocado and plants which bear tropical fruits, for example papaya, mango, but also pear, apple, nectarine, apricot or peach. Further examples of plants to be transformed are all types of cereals, rape, bird rape . . . The transformed cells are selected using a selection medium, cultured to a callus and regenerated to the plant on an appropriate medium (Shain M. et al., Theor. appl. Genet. 72, 770–770 (1986)); Masson, J. et al., Plant Science 53, 167–176 (1987)), Zhan X. et al., Plant Mol. Biol. 11, 551–559 (1988); McGranaham G. et al., Bio/Technology 6, 800–804 (1988); Novak F. J. et al., Bio/Technology 7, 154–159 (1989)).

The following examples serve to illustrate the invention further.

EXAMPLES

1. Isolation of the virus coat protein gene

The virus was purified by modification of the method of Lot, M. et al., Anual Phytopath. 4, 25–32 (1972). Alfalfa was infected with alfalfa mosaic virus and, after 14 days, disrupted in the same volume of 0.5M sodium citrate (pH 6.5)/5 mM EDTA/0.5% thioglycolic acid. Then 1 volume of chloroform was added, and the mixture was centrifuged at 12,000×g for 10 min. The supernatant was mixed with 10% PEG 6000 (w/w) and stirred cautiously overnight. It was then centrifuged at 12,000×g for 10 min and resuspended in 50 ml of 5 mM sodium borate, 0.5 mM EDTA (pH 9). Triton X-100 (final concentrations 2%) was added and then the mixture was stirred for 30 min and centrifuged at 19,000×g 2. Isolation of the herbicide-resistance gene A phosphinothricin-resistance gene with the following sequence (SEQ ID NO:1) and its component (SEQ ID NO:2) was synthesized in a synthesizer using the phosphoamidite method.

```
               9           18          27          36          45
5' GTC GAC ATG TCT CCG GAG AGG AGA CCA GTT GAG ATT AGG CCA GCT
3'     G TAC AGA GGC CTC TCC TCT GGT CAA CTC TAA TCC GGT CGA
              54          63          72          81          90
   ACA GCA GCT GAT ATG GCC GCG GTT TGT GAT ATC GTT AAC CAT TAC
   TGT CGT CGA CTA TAC CGG CGC CAA ACA CTA TAG CAA TTG GTA ATG
              99         108         117         126         135
   ATT GAG ACG TCT ACA GTG AAC TTT AGG ACA GAG CCA CAA ACA CCA
   TAA CTC TGC AGA TGT CAC TTG AAA TCC TGT CTC GGT GTT TGT GGT
             144         153         162         171         180
   CAA GAG TGG ATT GAT GAT CTA GAG AGG TTG CAA GAT AGA TAC CCT
   GTT CTC ACC TAA CTA GAT CTC TCC AAC GTT CTA TCT ATG GGA
             189         198         207         216         225
   TGG TTG GTT GCT GAG GTT GAG GGT GTT GTG GCT GGT ATT GCT TAC
   ACC AAC CAA CGA CTC CAA CTC CCA CAA CAC CGA CCA TAA CGA ATG
             234         243         252         261         270
   GCT GGG CCC TGG AAG GCT AGG AAC GCT TAC GAT TGG ACA GTT GAG
   CGA CCC GGG ACC TTC CGA TCC TTG CGA ATG CTA ACC TGT CAA CTC
             279         288         297         306         315
   AGT ACT GTT TAC GTG TCA CAT AGG CAT CAA AGG TTG GGC CTA GGA
   TCA TGA CAA ATG CAC AGT GTA TCC GTA GTT TCC AAC CCG GAT CCT
             324         333         342         351         360
   TCC ACA TTG TAC ACA CAT TTG CTT AAG TCT ATG GAG GCG CAA GGT
   AGG TGT AAC ATG TGT GTA AAC GAA TTC AGA TAC CTC CGC GTT CCA
             369         378         387         396         405
   TTT AAG TCT GTG GTT GCT GTT ATA GGC CTT CCA AAC GAT CCA TCT
   AAA TTC AGA CAC CAA CGA CAA TAT CCG GAA GGT TTG CTA GGT AGA
             414         423         432         441         450
   GTT AGG TTG CAT GAG GCT TTG GGA TAC ACA GCC CGG GGT ACA TTG
   CAA TCC AAC GTA CTC CGA AAC CCT ATG TGT CGG GCC CCA TGT AAC
             459         468         477         486         495
   CGC GCA GCT GGA TAC AAG CAT GGT GGA TGG CAT GAT GTT GGT TTT
   GCG CGT CGA CCT ATG TTC GTA CCA CCT ACC GTA CTA CAA CCA AAA
             504         513         522         531         540
   TGG CAA AGG GAT TTT GAG TTG CCA GCT CCT CCA AGG CCA GTT AGG
   ACC GTT TCC CTA AAA CTC AAC GGT CGA GGA GGT TCC GGT CAA TCC
             549         558
   CCA GTT ACC CAG ATC TGA G         3'
   GGT CAA TGG GTC TAG ACT CAG CTG 5'
``` for 15 min. The virus pellet after centrifugation at 105,000×g for 2 h was taken up in 5 mM borate buffer/0.5 mM EDTA (pH 9.0) and subjected to a sucrose centrifugation (5–25%).

Individual fractions from the gradient were analyzed on an agarose gel in order to find the virus-containing zone. The virus RNA was purified of coat protein by phenol/SDS extraction (Peden, K. W. et al., Virology 53, 487–492 (1973). The RNA components were fractionated using 2.8% polyacrylamide with 40 mM tris acetate buffer (pH 7.5) as described in Synous, R. H., Aust. J. Biol. Sci. 31, 25–37 (1978). The RNA was removed from the gel by electrophoresis in dialysis tubes and precipitated.

cDNA transcripts of RNA3 or RNA4 were prepared as described in Langenreis, K. et al., Plant Mol. Biol. 6, 281–288 (1986) using synthetic oligonucleotide primers with 3'-complementary nucleotides to the template, each of which had an SmaI or PstI cleavage site at the 5' end.

The reactions for the cDNA synthesis were carried out in accordance with the "Current Protocols in Mol. Biol." ed. Ausubel, F. et al., John Wiley and Sons.

The cDNA was cloned into the SmaI/PstI-cut pUC 19 vector. It was possible to delete the insertion again using SmaI/HindIII.

The method described above can equally be used to isolate the CMV coat protein gene.

This is a modification of the sequence for the acetyl-transferase gene published by Wohlleben in Gene 70, 25–37 (1988).

It is likewise possible to examine a genomic DNA bank from the *Streptomyces viridochromogenes* used by Wohlleben in EMBL3 in *E. coli* for the acetylation of phosphinothricin. The acetylated product can be very easily fractionated by thin-layer chromatography.

The gene was cloned in pUC19 and sequenced. Expression in plants was carried out as SalI fragment.

3. Fusion of herbicide-resistance gene with Nos promoter

The vector pNCN was digested with Bam/SalI, and the resulting 2.5 kb piece was isolated. The protruding ends were digested off with mung bean nuclease. The acetyltransferase gene was isolated as 0.5 kp piece after SalI digestion and filled in with Klenow. After ligase, it was possible to isolate positive clones by plasmid minipreparations. The orientation was evident from a SalI/Bam digestion.

4. Fusion of coat protein gene with 35S promoter

A fragment, 0.5 kb long, from pAI RNA3 (the pUC19 vector with coat protein gene insert) was isolated after digestion with SmaI/HindIII. The protruding ends were digested off by mung bean nuclease. The vector pDH 51 was cut with XbaI, and ends were filled in with Klenow polymerase. Fragment and vector were ligated and transformed into MC 1061 (p35/AI). The same construction was carried out with pCM RNA3 for the coat protein of CMV (p35/CM).

5. Fusion of 35S/coat protein gene and nos/acetyltransferase gene

A 1.3 kb piece from the 35S/coat protein construct (p35/AI, p35/CM) after EcoRI digestion was isolated from a low melt agarose gel. The plant vector pOCA 18 was digested with EcoRI and ligated to the 1.3 kbp DNA piece. This pOCA/35 RNA3 vector was filled in with Klenow. A 2.5 kbp HindIII piece from nos/AC was, after Klenow treatment of the ends, inserted into the filled-in ClaI site.

Constructions: pOCA/AcAI3
pOCA/AcCM3

6. Transformation of Agrobacteria

The *Agrobacterium* strain pMP90RK was transformed with pOCA/AcAI3 or pOCA/AcCM3 in triparental mating with SM10. 100 µl portions of bacteria from overnight cultures of SM10, the MC 1061 carrying the construction, and the Agrobacteria were spun down and suspended together in 30 µl of LB medium. These cells were placed on a small circular filter on an LB plate without antibiotic. After incubation at 37° C. for 12 h, the filter was washed in 2.5 ml of 10 mM MgCl$_2$, and aliquots thereof were selected on LB plates containing rifampicin, tetracycline and kanamycin. Positive colonies were identified by hybridization with $^{32}$P-labeled DNA of the genes.

7. Transformation of alfalfa

A modified version of the cocultivation method of Marton S. et al., Nature 277, 129–130 (1979) was employed for the transformation of alfalfa. Stalk sections about 1 cm long from sterile plants were placed in 40 ml of sterile MS medium in Erlenmeyer flasks, and 11 ml of a diluted overnight culture of the Agrobacteria ($5 \times 10^7$ cells/ml) were added. Incubation was continued at 25° C. for 3 days. The stalk segments were then washed three times with sterile water and placed on MS medium containing 300 mg/l carbamicillin and 100 mg/l kanamycin. A callus from which it was possible to regenerate whole plants formed after 3 weeks.

8. Testing of the plants

The plants showed, after working up of RNA and hybridization with radiolabeled DNA of the genes, expression of AC gene with alfalfa mosaic virus coat protein gene.

The plants grew on phosphinothricin-containing medium and showed distinct tolerance after infection with alfalfa mosaic virus.

We claim:

1. An isolated DNA molecule consisting of a nucleotide sequence coding region for a phosphinothricin acetyl transferase protein which confers phosphinothricin resistance and a nucleotide sequence coding region for a virus coat protein which confers virus resistance.

2. An isolated DNA molecule as claimed in claim 1, wherein the nucleotide coding region for the virus coat protein which confers virus resistance is obtained by cDNA cloning starting from RNA of cucumber mosaic virus, alfalfa mosaic virus or brome mosaic virus.

3. An isolated DNA molecule as claimed in any one of claims 1 or 2 wherein the nucleotide coding region for the phosphinothricin acetyl transferase protein is from *Streptomyces*.

4. A host cell containing an isolated DNA molecule as claimed in claim 3, which expresses the proteins.

5. A host cell containing an isolated DNA molecule as claimed in any one of claims 1 or 2, which expresses the proteins.

6. Plants, plant cells, or seeds of plants containing the isolated DNA molecule as claimed in any of claims 1 or 2, and which express the proteins.

7. Plants, plant cells, or seeds of plants containing the isolated DNA molecule of claim 3, and which express the proteins.

8. A host cell containing the isolated DNA molecule of claim 2, wherein the nucleotide coding region for the phosphinothricin acetyl transferase protein is from *Streptomyces* and the cell expresses the proteins.

9. Plants, plant cells or plant seeds containing the cell of claim 8.

10. A transformed plant cell containing and expressing an isolated DNA molecule consisting of a nucleotide sequence coding region for a phosphinothricin acetyl transferase protein which confers phosphinothricin resistance and, an isolated DNA molecule consisting of a nucleotide sequence coding region for a virus coat protein which confers virus resistance.

11. A method for improving growth of a plant comprising: transforming plant cells so that the cells contain an isolated DNA molecule consisting of a nucleotide sequence coding region for a phosphinothricin acetyl transferase protein which confers phosphinothricin resistance and, an isolated DNA molecule consisting of a nucleotide sequence coding region for a virus coat protein which confers virus resistance; selecting transformed cells; regenerating plants from the cells; and treating the regenerated plants with a phosphinothricin herbicide.

12. The cell of claim 10 wherein the virus is cucumber, alfalfa or brome mosaic virus.

13. The cell of claims 10, or 12 wherein the isolated DNA molecule consisting of a nucleotide sequence coding region for the phosphinothricin acetyl transferase protein is from *Streptomyces*.

14. A method for improving growth of a plant comprising regenerating the plant from the cell as claimed in claims 10, or 12 and treating the regenerated plant with a phosphinothricin herbicide.

15. A method for improving grouch of a plant comprising regenerating the plant from the cell of claim 13, and treating the regenerated plant with a phosphinothricin herbicide.

16. The method of claim 11 wherein the virus is cucumber, alfalfa or brome mosaic virus.

17. The method of claims 11, or 16 wherein the coding region for the phosphinothricin acetyl transferase protein is from *Streptomyces*.

18. A plant, or plant seed containing the cell of claim 10, or 12.

19. A plant, or plant seed containing the cell of claim 13.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 559 base pairs
( B ) TYPE: nucleic acid
( C ) STRANDEDNESS: single
( D ) TOPOLOGY: linear ( x i ) SEQUENCE DESCRIPTION: SEQ ID NO:1:

```
GTCGACATGT CTCCGGAGAG GAGACCAGTT GAGATTAGGC CAGCTACAGC AGCTGATATG      60
GCCGCGGTTT GTGATATCGT TAACCATTAC ATTGAGACGT CTACAGTGAA CTTTAGGACA     120
GAGCCACAAA CACCACAAGA GTGGATTGAT GATCTAGAGA GGTTGCAAGA TAGATACCCT     180
TGGTTGGTTG CTGAGGTTGA GGGTGTTGTG GCTGGTATTG CTTACGCTGG GCCCTGGAAG     240
GCTAGGAACG CTTACGATTG GACAGTTGAG AGTACTGTTT ACGTGTCACA TAGGCATCAA     300
AGGTTGGGCC TAGGATCCAC ATTGTACACA CATTTGCTTA AGTCTATGGA GGCGCAAGGT     360
TTTAAGTCTG TGGTTGCTGT TATAGGCCTT CCAAACGATC CATCTGTTAG GTTGCATGAG     420
GCTTTGGGAT ACACAGCCCG GGGTACATTG CGCGCAGCTG GATACAAGCA TGGTGGATGG     480
CATGATGTTG GTTTTTGGCA AAGGGATTTT GAGTTGCCAG CTCCTCCAAG GCCAGTTAGG     540
CCAGTTACCC AGATCTGAG                                                  559
```

( 2 ) INFORMATION FOR SEQ ID NO:2:

( i ) SEQUENCE CHARACTERISTICS:
( A ) LENGTH: 559 base pairs
( B ) TYPE: nucleic acid
( C ) STRANDEDNESS: single
( D ) TOPOLOGY: linear ( x i ) SEQUENCE DESCRIPTION: SEQ ID NO:2:

-continued

```
GTCGACTCAG ATCTGGGTAA CTGGCCTAAC TGGCCTTGGA GGAGCTGGCA ACTCAAAATC     60
CCTTTGCCAA AAACCAACAT CATGCCATCC ACCATGCTTG TATCCAGCTG CGCGCAATGT    120
ACCCCGGGCT GTGTATCCCA AAGCCTCATG CAACCTAACA GATGGATCGT TTGGAAGGCC    180
TATAACAGCA ACCACAGACT TAAAACCTTG CGCCTCCATA GACTTAAGCA AATGTGTGTA    240
CAATGTGGAT CCTAGGCCCA ACCTTTGATG CCTATGTGAC ACGTAAACAG TACTCTCAAC    300
TGTCCAATCG TAAGCGTTCC TAGCCTTCCA GGGCCCAGCG TAAGCAATAC CAGCCACAAC    360
ACCCTCAACC TCAGCAACCA ACCAAGGGTA TCTATCTTGC AACCTCTCTA GATCATCAAT    420
CCACTCTTGT GGTGTTTGTG GCTCTGTCCT AAAGTTCACT GTAGACGTCT CAATGTAATG    480
GTTAACGATA TCACAAACCG CGGCCATATC AGCTGCTGTA GCTGGCCTAA TCTCAACTGG    540
TCTCCTCTCC GGAGACATG                                                 559
```